United States Patent
Haake et al.

(10) Patent No.: US 6,743,956 B1
(45) Date of Patent: Jun. 1, 2004

(54) SELECTIVE LIQUID PHASE HYDROGENATION OF CARBONYL COMPOUNDS TO GIVE THE CORRESPONDING ALCOHOLS IN THE PRESENCE OF A PT/ZNO CATALYST

(75) Inventors: Mathias Haake, Mannheim (DE); Till Gerlach, Ludwigshafen (DE); Frank Funke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/309,255

(22) Filed: Dec. 4, 2002

(30) Foreign Application Priority Data

Dec. 7, 2001 (DE) .......................... 101 60 141

(51) Int. Cl.[7] .............................. C07C 27/00
(52) U.S. Cl. ................ 568/903; 568/813; 568/875; 568/824; 568/880; 564/422
(58) Field of Search .................. 568/903, 813, 568/875, 824, 880; 564/422

(56) References Cited

U.S. PATENT DOCUMENTS

| | | | |
|---|---|---|---|
| 4,073,813 A | 2/1978 | Cordier ...................... 260/617 |
| 4,100,180 A | 7/1978 | Ichikawa et al. | |
| 4,465,787 A | 8/1984 | Horner et al. | |
| 5,118,884 A | 6/1992 | Didillon et al. ............. 568/875 |
| 5,939,589 A | 8/1999 | Kaibel et al. | |
| 6,150,564 A | 11/2000 | Broecker et al. | |
| 6,294,696 B1 | 9/2001 | Didillon et al. ............. 564/422 |

FOREIGN PATENT DOCUMENTS

| | | |
|---|---|---|
| DE | 2650046 | 5/1977 |
| EP | 071 787 | 2/1983 |
| EP | 422 968 | 4/1991 |
| EP | 947 493 | 10/1999 |

OTHER PUBLICATIONS

Consonni et al, Journal of Catalysts, v 188, pp 165–175, 1999.*
J. Chem. Tech. Biotechnol. 1994, 60, 83–88, Neri et al.

Recchia et al., *J. of Catalysis,* 184, 1999, pp. 1–4.
Paulose et al., *J. of Oil Tech. Assoc. of India,* 1974, p. 88–91.

\* cited by examiner

Primary Examiner—Hector M. Reyes
(74) Attorney, Agent, or Firm—Keil & Weinkauf

(57) ABSTRACT

The present invention relates to a process for selective liquid phase hydrogenation of carbonyl compounds of the general formula I,

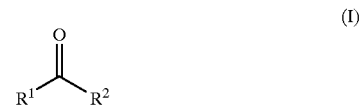

(I)

where $R^1$ and $R^2$ are identical or different and are each independently hydrogen or a saturated or a mono- or polyunsaturated straight-chain or branched, optionally substituted $C_1$–$C_{20}$-alkyl radical, an optionally substituted aryl radical or an optionally substituted heterocyclic group, to give the corresponding alcohols of the general formula II

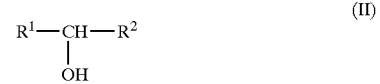

(II)

where $R^1$ and $R^2$ are each as defined above, in the presence of hydrogen and a Pt/ZnO catalyst.

17 Claims, No Drawings

SELECTIVE LIQUID PHASE HYDROGENATION OF CARBONYL COMPOUNDS TO GIVE THE CORRESPONDING ALCOHOLS IN THE PRESENCE OF A PT/ZNO CATALYST

The present invention relates to a process for the selective liquid phase hydrogenation of carbonyl compounds to give the corresponding alcohols, especially of citral to give geraniol/nerol or of citronellal to give citronellol, with hydrogen in the presence of a Pt/ZnO catalyst.

The prior art discloses various hydrogenation processes for α,β-unsaturated carbonyl compounds. It is very difficult to obtain high selectivities for the corresponding unsaturated alcohols. The hydrogenation of citral can lead to the hydrogenation of the olefinic double bonds as well as the aldehyde group, or only of the double bond conjugated to the aldehyde group, so that as well as the unsaturated alcohols geraniol or nerol, byproducts such as citronellol or citronellal can be formed.

U.S. Pat. No. 4,100,180 describes a process for the hydrogenation of unsaturated aldehydes to give unsaturated alcohols in the presence of a PtO/Zn/Fe catalyst. PtO powder is doped with Zn and Fe (suspension catalyst). In the citral hydrogenation with a citral conversion of 70%, 3.2% citronellol is obtained. In the reaction effluents, up to 25 ppm of Fe and Zn compounds are found. If the catalyst is reused, small amounts of Fe and Zn compounds must be added. The citronellol selectivities are unsatisfactorily high and additionally the use of PtO is very expensive and makes theprocess uneconomical.

Neri et al. (J. Chem. Tech. Biotechnol. 60 (1994), 83–88) describe a selective hydrogenation process of citral over a Pt—Sn catalyst on activated carbon. The production of the catalyst is carried out by simultaneous impregnation of the activated carbon by Pt and Sn with the use of chlorides. The citral hydrogenation is carried out in ethanol as the solvent. The addition of tin improves the activity and also the selectivity. However, the citronellol selectivities are greater than 5%.

EP 071 787 discloses ruthenium/carbon hydrogenation catalysts, and their preparation and use for selective hydrogenation of unsaturated carbonyl compounds. The Ru/Fe/C catalyst is prepared by doping of activated carbon with ruthenium chloride hydrate, drying and mixing with iron oxide powder and reduction at 500° C. Methanol and trimethylamine are added to the catalytic reaction to improve the selectivity. The selectivities are 2.3% for citronellol and 96.5% for geraniol/nerol at 100% conversion. However, the addition of methanol and trimethylamine makes an additional separation step during the workup of the reaction effluents necessary.

EP 422 968 describes the hydrogenation of citral with an $SiO_2$-supported catalyst, which contains 0.1 to 10% by weight of Ir, Pt, Rh or Ru as the active component and is doped with 0.01 to 10% by weight tin, lead or germanium. The reaction is carried out in hexane. The citronellol selectivities obtained are greater than 3.5%.

In the prior art procedures for the hydrogenation of α,β-unsaturated carbonyl compounds the selectivity to give unsaturated alcohols is not satisfactory. Particularly during the hydrogenation of citral with high citral conversions the selectivity to give citronellol is over 2%. Since citronellol/nerol mixtures are very difficult to separate by distillation, this limits their industrial utility significantly. An advantageous catalyst shall allow citronellol selectivities below 2% even at citral conversions greater than 95%.

The prior art procedures frequently involve solvents, sometimes even with the addition of auxiliaries such as trimethylamine. This increases the cost and inconvenience of the distillative workup. Furthermore the reactor volume is increased, which considerably detracts from the economic viability of the process.

It is an object of the present invention to develop an improved process for the hydrogenation of carbonyl compounds to give the corresponding alcohols, in particular for the hydrogenation of citral to give geraniol/nerol or of citronellal to give citronellol, that at high citral conversions gives low citronellol selectivities in an economical manner.

We have found that this object is achieved by a process for selective liquid phase hydrogenation of carbonyl compounds of the general formula I

where
$R^1$ and $R^2$ are identical or different and are each independently hydrogen or a saturated or a mono- or polyunsaturated straight-chain or branched, optionally substituted $C_1$–$C_{20}$-alkyl radical, an optionally substituted aryl radical or an optionally substituted heterocyclic group, to give the corresponding alcohols of the general formula II

where $R^1$ and $R^2$ are each as defined above,
in the presence of hydrogen and a Pt/ZnO catalyst.

The catalyst hydrogenates the aldehyde group of the unsaturated carbonyl compound with surprisingly high selectivity.

A singly or multiply unsaturated straight chain or branched $C_1$–$C_{10}$-alkyl radical is, unless otherwise stated, a methyl, ethyl, propyl, isopropyl, n-butyl, i-butyl, t-butyl, pentyl, hexyl, heptenyl, octyl, nonyl, decyl, 1-propenyl, 2-propenyl, 2-methyl-2-propenyl, 1-pentenyl, 1-methyl-2-pentenyl, isopropenyl, 1-butenyl, hexenyl, heptenyl, octenyl, nonenyl, or a decenyl radical or the radicals corresponding to the compounds used listed below.

A $C_1$–$C_4$-alkyl radical is, unless otherwise stated, a methyl, ethyl, propyl, i-propyl, butyl or t-butyl radical.

An aryl radical is a benzyl, phenyl or naphthyl radical.

A heterocyclic group is, for example, a pyridine, pyrimidine, pyridazine, pyrazine, piperazine, imidazole, furan, oxazole, isothiazole, isoxazole, 1,2,3-, 1,2,4-triazole, thiazole, thiophene or indole ring.

Substituents can be methyl, ethyl, propyl, i-propyl, butyl, t-butyl, fluorine, chlorine, bromine, iodine, nitro or amino.

Examples of useful saturated carbonyl compounds include 3,7-dimethyloctan-1-al and its isomers, tetrahydrogeranylacetone, hexahydrofarnesylacetone, 6-methylheptanone and isovaleraldehyde.

Examples of useful olefinically unsaturated carbonyl compounds include citronellal, H-geranylacetone, H-nerolidol, methyl vinyl ketone, mesityl oxide, pseudoionone, dihydrofarnesylacetone, lysmeral, methylhexenone, particularly preferably citronellal or else α,β-unsaturated carbonyl compounds, for example acrolein, methacrolein, crotonaldehyde, prenal, farnesal or citral, more preferably citral.

A preferred embodiment of the process involves the conversion of citral to geraniol or nerol, or of citronellal to citronellol.

The Pt/ZnO catalyst employed can be used as an unsupported catalyst or else, to improve the mechanical stability, as a supported catalyst. Suitable supporting materials include all usual supporting materials, for example, γ-$Al_2O_3$, α-$Al_2O_3$, $SiO_2$, activated carbon, $TiO_2$, $ZrO_2$, zeolites or monolithic packing structures.

However, the catalyst is preferably used as an unsupported catalyst.

The process can be carried out continuously or else batchwise in suspension or in a fixed bed. The continuous method is particularly advantageous.

The suspension or fixed bed variant may be carried out in the usual reactor designs, as described, for example, in Ullmann's Encyclopedia of Industrial Chemistry, Sixth Edition, 2000 Electronic Release.

The continuous or batchwise suspension process can be carried out as described in EP 947 943 or U.S. Pat. No. 5,939,589. The catalyst is used in both the batchwise and the continuous suspension method in finely divided form, with a particle size of less than 1 mm, preferably in the range from 1 to 100 μm.

The fixed bed variant includes the use of the catalyst in extruded or spall form. Typical extruded diameters lie in the range from 1 to 5 mm, the extruded lengths in the range from 1 to 20 mm. The reactor can be operated using trickle or liquid phase methods.

The reaction is carried out in both the suspension and the fixed bed methods at atmospheric or at a pressure in the range from 1 to 200 bar, preferably 10 to 100 bar, particularly preferably 20 to 50 bar. The temperatures are in the range from 25 to 200° C., preferably from 80 to 150° C. The reaction can be carried out with or without a solvent. Suitable solvents include lower alcohols such as methanol, ethanol or isopropyl alcohol. Furthermore, an organic base such as trimethylamine can be used if necessary. However, the process is preferably carried out without the use of a solvent or an additional base.

The Pt/ZnO catalyst employed contains 0.1–10% by weight of Pt, preferably 2–8% by weight, the BET surface area is from 1 to 30 $m^2/g^{-1}$ and the Pt particle size is from 1 to 10 nm. The platinum particles undergo partial agglomeration to give agglomerates of a size of from 10 to 100 nm.

The following examples illustrate the invention.

EXAMPLE

Catalyst Production

Unsupported Catalyst 200 g ZnO extrudates of 4 mm diameter were saturated with an aqueous solution of hexachloroplatinic acid [$H_2PtCl_6xH_2O$]. To do this, 20.9 g of hexachloroplatinicacid were dissolved in 56 g of distilled water. The damp extrudates were dried at 120° C. and then heat treated at 400° C. for 4 h. The catalyst was then installed in a reduction column and reduced at 200° C. for 2 h. Before removal from the reduction column the catalyst was passivated at room temperature in a diluted airstream. Before the autoclave tests the catalyst was ground to a particle size of less than 100 μm.

The catalyst prepared in this way had a Pt content of 5.3% by weight and a chlorine content of 1.5% by weight.

Supported Catalyst

To prepare a supported catalyst the support is first saturated with Zn salts such as $Zn(NO_3)_2$ or $ZnCl_2$ and by subsequent drying at 120° C. (50–200° C.), 1–6 h, and calcining at 200–500° C. (1–6 h), the Zn salt is converted to ZnO, which is then in state of firm attachment to the support. The support can then be saturated with Pt in the form of $H_2PtCl_6$, dried, calcined and reduced, in the same way as during the production of the unsupported catalyst.

The ZnO content of the catalyst is in the range from 1 to 90% by weight, the Pt content in the range from 0.1 to 10% by weight.

Catalyst Testing

Inventive Example 1

5 g of the unsupported catalyst powder were introduced into an autoclave of 300 ml volume. To this were added 250 ml of citral, i.e. a mixture of about 50% geranial and 50% neral. After sealing of the autoclave it was heated to 140° C. with stirring and under nitrogen. After the final temperature was reached the nitrogen was replaced by hydrogen and this was pressurized to 50 bar. The reaction was run using an off-gas rate of 50 l/h.

In this test the results in table 1 were obtained as a function of the reaction time.

TABLE 1

| Reaction time/min | 120 | 240 | 360 | 480 | 600 | 720 | 840 | 900 |
|---|---|---|---|---|---|---|---|---|
| Citral conversion % | 10.5 | 24.0 | 45.7 | 70.5 | 90.7 | 99.0 | 99.3 | 99.4 |
| Selectivities % | | | | | | | | |
| citronellal | 1.9 | 1.3 | 0.8 | 0.4 | 0.2 | 0.0 | 0.0 | 0.0 |
| citronellol | 0.4 | 0.4 | 0.6 | 0.9 | 1.1 | 1.4 | 1.5 | 1.5 |
| nerol | 20.6 | 29.8 | 32.7 | 33.6 | 34.1 | 35.4 | 35.5 | 35.1 |
| geraniol | 27.5 | 43.4 | 50.4 | 52.4 | 52.7 | 53.0 | 52.8 | 52.2 |
| Unknown | 20.4 | 12.9 | 9.6 | 9.5 | 9.3 | 8.1 | 8.2 | 9.1 |

Inventive Example 2 (Fixed Bed)

A continuous laboratory apparatus (reactor geometry: length 171 mm/diameter: 27.3 mm/100 ml reactor capacity, straight pass operation) was charged with the extruded unsupported catalyst and the reactor was purged with hydrogen (20 l/h, STP). The reactor was then pressurized with hydrogen to 20 bar. The temperature was increased to the reaction temperature and the pressure increased to 40 bar. The reactant was passed over the catalyst at different temperatures (60–150° C.) and different space velocities (0.2–0.6 kg/l*h) in a liquid phase process. The product was depressurized into a stock container and analyzed by gas chromatography (50 m DB1 0.24 mm 0.4 micrometer, 130° C.-1° C./min- 155° C.-20° C./min-280° C.).

The results listed in table 2 were obtained:

TABLE 2

| T/° C. | Space velocity kg/l/h | Conversion | Selectivities Citronellol | Nerol | Geraniol |
|---|---|---|---|---|---|
| 100 | 0.4 | 70 | 0.58 | 43 | 49 |
| 120 | 0.4 | 93 | 1.1 | 45 | 46 |

Inventive Example 3

A recirculation apparatus using a liquid phase method was chosen. After the reduced-passivated catalyst had been introduced to the tube reactor, the apparatus was charged with 0.55 liter of citral. After pressurizing with hydrogen to 50 bar the circulation pump was switched on and a cross-sectional velocity of 100 m³/m²/h, based on the free reactor cross section, was set. Using a preheater the reactor inlet temperature was set to 120° C. During the hydrogenation samples were taken from the circulation at regular intervals and analyzed by gas chromatography. An off-gas stream of 50 l/h was set permanently, in order to keep the CO content below 10 ppm during the entire operation.

| Citral | Nerol | Geraniol | Citronellal | Isopulegol | Citronellol | Byproducts above retention time 43.5 | Conversion | Selectivity | Yield | CO in off-gas |
|---|---|---|---|---|---|---|---|---|---|---|
| 96.33 | 0.12 | 0.13 | 0.03 | 1.77 | 0.01 | <0.5 | 0 | 0 | 0 | 0 |
| 91.93 | 2.18 | 2.60 | 0.16 | 1.34 | 0.05 | <0.5 | 4.57 | 100.00 | 4.57 | 16 |
| 82.48 | 6.27 | 7.30 | 0.25 | 1.47 | 0.11 | <0.5 | 14.38 | 97.98 | 14.09 | 11 |
| 73.53 | 10.37 | 11.92 | 0.32 | 1.43 | 0.19 | <0.5 | 23.67 | 97.76 | 23.14 | 9 |
| 65.21 | 14.11 | 15.94 | 0.38 | 1.49 | 0.27 | <0.5 | 32.31 | 96.56 | 31.19 | 8 |
| 50.12 | 21.43 | 23.50 | 0.45 | 1.26 | 0.48 | <0.5 | 47.97 | 97.23 | 46.64 | 8 |
| 45.51 | 23.57 | 25.36 | 0.49 | 1.36 | 0.58 | 0.51 | 52.76 | 96.28 | 50.79 | 7.0 |
| 39.93 | 26.32 | 28.11 | 0.48 | 1.17 | 0.69 | 0.61 | 58.55 | 96.51 | 56.50 | 8.5 |
| 18.13 | 37.71 | 38.25 | 0.39 | 0.70 | 1.22 | 0.77 | 81.18 | 97.14 | 78.85 | 9 |
| 6.70 | 44.32 | 43.10 | 0.21 | 0.37 | 1.65 | 0.74 | 93.04 | 97.53 | 90.75 | 9 |
| 2.07 | 47.26 | 44.86 | 0.11 | 0.21 | 1.92 | 0.65 | 97.85 | 97.73 | 95.63 | 8 |
| 0.65 | 48.25 | 45.34 | 0.30 | 0.14 | 2.07 | 0.57 | 99.33 | 97.82 | 97.16 | 8 |
| 0.30 | 48.54 | 45.52 | 0.04 | 0.13 | 2.16 | 0.51 | 99.69 | 97.95 | 97.64 | 7 |

Results in GC area %, CO content in ppm
From this table it can be seen that with the catalyst of the invention a total geraniol/nerol yield of >97% with only 2% of citronellol can be obtained even at high citral conversions >99%.

| | | | | Comparative examples to inventive example 3 | | | | | | |
|---|---|---|---|---|---|---|---|---|---|---|
| Run No. | Catalyst | T ° C. | P bar | Citral cis/trans area % | Nerol area % | Geraniol area % | Citronellal area % | Citronellol area % | Conversion % | Selectivity % |
| 1 | Ru/Al₂O₃ | 100 | 50 | 19.67 | 21.51 | 30.40 | 5.96 | 18.76 | 79.55 | 67.84 |
| 2 | Pt/Al₂O₃ | 100 | " | 82.09 | 1.98 | 2.67 | 1.23 | 4.77 | 4.93 | 26.29 |
| 3 | Cu/Cr Al₂O₃ | 175 | " | 37.57 | 12.34 | 18.29 | 15.62 | 7.16 | 61.45 | 51.14 |

We claim:

1. A process for liquid phase hydrogenation of carbonyl compounds comprising reacting in the liquid phase a carbonyl compound of the formula I

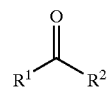

(I)

where

R¹ and R² are identical or different and are each independently hydrogen or a saturated or a mono- or polyunsaturated straight-chain or branched, optionally substituted $C_1$–$C_{20}$-alkyl radical, an optionally substituted aryl radical or an optionally substituted heterocyclic group, in the presence of hydrogen and a Pt/ZnO catalyst, to give the corresponding alcohol of the formula II

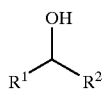

(II)

where $R^1$ and $R^2$ are each as defined above.

2. The process as claimed in claim 1, wherein the carbonyl compound is an α,β-unsaturated carbonyl compound.

3. The process as claimed in claim 1 or 2, wherein the carbonyl compound is citral.

4. The process as claimed in claim 1, wherein the carbonyl compound is citronellal.

5. The process as claimed in claim 4, wherein the citronellol selectivity is under 2% even in conversions>95%.

6. The process as claimed in claim 1 carried out in a continuous manner.

7. The process as claimed in claim 1, wherein the Pt/ZnO catalyst is used in a supported or unsupported form.

8. The process as claimed in claim 1, wherein the process is carried out in suspension.

9. The process as claimed in claim 1, wherein the particle size of the catalyst is smaller than 1 mm.

10. The process as claimed in claim 1, wherein the process is carried out in a fixed bed.

11. The process as claimed in claim 10, wherein the catalyst is used in extruded form.

12. The process as claimed in claim 1, wherein the process is carried out at atmospheric pressure or at a pressure of from 10 to 100 bar.

13. The process as claimed in claim 1, wherein the process is carried out at from 25 to 200° C.

14. The process as claimed in claim 1, wherein the Pt/ZnO catalyst contains from 0.1 to 10% by weight of Pt.

15. The process as claimed in claim 1, wherein the Pt particle size of the catalyst employed is in the range from 1 to 10 nm.

16. The process as claimed in claim 1, wherein the CO content is held below 100 ppm by adjusting an off-gas stream.

17. The process as claimed in claim 1, wherein the CO content is held below 10 ppm by adjusting an off-gas stream.

* * * * *